(12) United States Patent
Ashraf et al.

(10) Patent No.: US 7,445,831 B2
(45) Date of Patent: Nov. 4, 2008

(54) RADIATION CURABLE LOW STRESS RELAXATION ELASTOMERIC MATERIALS

(75) Inventors: Arman Ashraf, Hamilton, OH (US); Yan Zhao, Ames, IA (US)

(73) Assignee: The Procter & Gamble Company, Cincinnati, OH (US)

( * ) Notice: Subject to any disclaimer, the term of this patent is extended or adjusted under 35 U.S.C. 154(b) by 282 days.

(21) Appl. No.: 10/610,605

(22) Filed: Jul. 1, 2003

(65) Prior Publication Data

US 2004/0049836 A1 Mar. 18, 2004

Related U.S. Application Data

(60) Provisional application No. 60/393,498, filed on Jul. 3, 2002.

(51) Int. Cl.
*B32B 3/24* (2006.01)
*A41D 13/12* (2006.01)
*C08G 2/00* (2006.01)
*C08F 2/46* (2006.01)

(52) U.S. Cl. .................. 428/138; 428/132; 428/131; 264/477; 2/456; 522/6; 522/35

(58) Field of Classification Search .............. 428/138, 428/132, 131; 522/6, 35; 264/477; 2/456
See application file for complete search history.

(56) References Cited

U.S. PATENT DOCUMENTS

| | | | |
|---|---|---|---|
| 3,860,003 A | 1/1975 | Buell | |
| 3,929,135 A | 12/1975 | Thompson | |
| 4,133,731 A | 1/1979 | Hansen et al. | |
| 4,152,387 A | 5/1979 | Cloeren | |
| 4,154,240 A | 5/1979 | Ikuno et al. | |
| 4,163,664 A | 8/1979 | Ugo | |
| 4,197,069 A | 4/1980 | Cloeren | |
| 4,342,314 A | 8/1982 | Radel et al. | |
| 4,381,781 A | 5/1983 | Sciaraffa et al. | |
| 4,533,308 A | 8/1985 | Cloeren | |
| 4,552,709 A | 11/1985 | Koger, II et al. | |
| 4,556,464 A | 12/1985 | St. Clair | |
| 4,695,422 A | 9/1987 | Curro et al. | |
| 4,716,183 A | 12/1987 | Gamarra et al. | |
| 4,741,877 A | 5/1988 | Mullane, Jr. | |
| 4,857,067 A | 8/1989 | Wood et al. | |
| 4,878,825 A | 11/1989 | Mullane, Jr. | |
| 4,938,753 A | 7/1990 | Van Gompel et al. | |
| 5,073,611 A | 12/1991 | Rehmer et al. | |
| 5,143,679 A | 9/1992 | Weber et al. | |
| 5,151,092 A | 9/1992 | Buell et al. | |
| 5,156,793 A | 10/1992 | Buell et al. | |
| 5,167,897 A | 12/1992 | Weber et al. | |
| 5,221,274 A | 6/1993 | Buell et al. | |

(Continued)

FOREIGN PATENT DOCUMENTS

WO    WO 93/16131 A1    8/1993

(Continued)

*Primary Examiner*—William P Watkins, III
(74) *Attorney, Agent, or Firm*—Dara M. Kendall; John P. Colbert

(57) ABSTRACT

A radiation-curable low stress relaxation elastomeric material with improved elastic and mechanical properties. The elastomeric material may be used alone or with skin layers to form elastomeric films, webs, laminates and products containing them.

24 Claims, 4 Drawing Sheets

U.S. PATENT DOCUMENTS

| | | |
|---|---|---|
| 5,246,433 A | 9/1993 | Hasse et al. |
| 5,407,717 A | 4/1995 | Lucast et al. |
| 5,407,971 A | 4/1995 | Everaerts et al. |
| 5,459,174 A * | 10/1995 | Merrill et al. ............... 522/35 |
| 5,464,401 A | 11/1995 | Hasse et al. |
| 5,468,821 A | 11/1995 | Lucast et al. |
| 5,518,801 A | 5/1996 | Chappell et al. |
| 5,554,145 A | 9/1996 | Roe et al. |
| 5,569,234 A | 10/1996 | Buell et al. |
| 5,580,411 A | 12/1996 | Nease et al. |
| 5,628,097 A | 5/1997 | Benson et al. |
| 5,650,214 A | 7/1997 | Anderson et al. |
| 5,669,897 A | 9/1997 | Lavon et al. |
| 5,733,628 A | 3/1998 | Pelkie |
| 5,897,545 A | 4/1999 | Kline et al. |
| 6,004,306 A | 12/1999 | Robles et al. |
| 6,120,487 A | 9/2000 | Ashton |
| 6,294,698 B1 | 9/2001 | Nohr et al. |
| 6,303,208 B1 | 10/2001 | Pelkie |
| 6,369,123 B1 | 4/2002 | Stark et al. |
| 6,384,139 B1 | 5/2002 | Ho et al. |
| 6,586,354 B1 * | 7/2003 | Topolkaraev et al. ........ 442/394 |
| 2003/0105232 A1 * | 6/2003 | Zhao et al. ............... 525/191 |

FOREIGN PATENT DOCUMENTS

| | | |
|---|---|---|
| WO | WO 98/37266 A1 | 8/1998 |
| WO | WO 99/64931 A1 | 12/1999 |
| WO | WO 01/19918 | 3/2001 |
| WO | WO 01/19920 | 3/2001 |
| WO | WO 02/20625 | 3/2002 |

* cited by examiner

RADIATION CURABLE LOW STRESS RELAXATION ELASTOMERIC MATERIALS

CROSS REFERENCE TO RELATED APPLICATION

This application claims the benefit of U.S. Provision Application No. 60/393,498, filed Jul. 3, 2002.

FIELD OF THE INVENTION

The present invention relates to low stress relaxation elastomeric compositions and products made from them. In one aspect, the invention relates to selective crosslinking of the elastomeric compositions using functionalized macromolecular crosslinking agents to provide improved mechanical and elastic properties. In another aspect, the invention relates to processes for making melt processable and radiation curable elastomeric compositions into products, such as substantially planar films; macroscopically-expanded, three-dimensional webs; apertured webs; laminates of the films or webs; and absorbent articles with components made from such films, webs or laminates.

BACKGROUND OF THE INVENTION

Elastomeric block copolymers having vinylarene polymer blocks and olefinic and/or diene polymer blocks typically exhibit a bi-phasic morphology, in which similar blocks come together to form one phase distinct from a second phase formed by the other blocks. The block copolymers form a three-dimensional, entangled (i.e., physical crosslinks) network structure. The polymeric chains may move about and disentangle from those physical crosslinks, resulting in loss of elastic and mechanical properties. Low molecular weight crosslinking agents have been used to create chemical crosslinks among polymeric chains to improve properties. However, it is known that small molecules are thermodynamically more compatible, thus, less selective, with respect to both phases of the bi-phasic copolymers. Consequently, low molecular weight crosslinking agents are intimately mixed with both phases of the copolymers and crosslinks indiscriminately in both phases. The resulting materials may become more difficult to process and more brittle in use. Approaches to selectively crosslink one phase are also known. Elastomeric compositions containing general and selective crosslinking agents are disclosed in U.S. Pat. No. 4,133,731 (Hansen et al.); U.S. Pat. No. 4,556,464 (St. Claire); U.S. Pat. No. 5,073,611 (Rehmer et al.); U.S. Pat. No. 5,407,971 (Everaerts et al.); U.S. Pat. No. 6,294,698 (Nohr et al.); U.S. Pat. No. 6,369,123 (Stark et al.); and U.S. Pat. No. 6,384,139 (Ho et al.).

There is a continuing need for curable elastomeric compositions that are selectively crosslinked to provide improved elastic and mechanical properties and still maintain the processability of thermoplastics.

Elasticized portions of health care or personal hygiene products are conformable to the body, and create a relatively occlusive environment under the products. As materials with greater elasticity are used in such products to provide a better fit to the body, the air flow to the skin and the vapor flow from the occluded areas are reduced. Breathability (particularly vapor permeability) becomes an important factor for skin health. Several methods for rendering elastomeric materials more porous and more breathable are known in the art, such as die punching, slitting, and hot-pin aperturing. Improved methods to produce better porous films or webs, such as macroscopically-expanded, three-dimensional webs, are disclosed in U.S. Pat. No. 3,929,135 (Thompson); U.S. Pat. No. 4,342,314 (Radel et al.); U.S. Pat. No. 5,733,628 (Pelkie); U.S. Pat. No. 6,303,208 (Pelkie); and PCT Publication WO 98/37266 (Curro et al.).

There is considerable difficulty in processing and handling elastomeric materials, due to the inherent tacky and stretchy nature of the elastomeric materials. The elastomeric materials have a tendency, to stick to the processing equipment, and are difficult to remove from a roll or cut to the correct size to be incorporated into the finished products. Further, the elastomeric materials may be joined to non-elastomeric substrates, such as inelastic nonwoven materials, and means to impart elasticity to the resulting laminates are desirable. Various processes for imparting elasticity are disclosed in U.S. Pat. No. 4,153,664 (Sabee); U.S. Pat. No. 5,143,679 (Weber et al.); U.S. Pat. No. 5,156,793 (Buell et al.); U.S. Pat. No. 5,167,897 (Weber et al.); U.S. Pat. No. 5,518,801 (Chappell et al.); U.S. Pat. No. 5,628,097 (Benson et al.); U.S. Pat. No. 5,650,214 (Anderson et al.). However, various elastomeric materials are known to suffer defects, such as pinholes, fisheyes, or the like, under the above processes or combinations thereof. Such defects in the elastomeric materials may act as stress concentrators that promote tear initiation, tear propagation and catastrophic failure of the materials during use.

Therefore, there is a continuing need for elastomeric materials that provide elasticity (including low stress relaxation) and breathability as well as processability.

It is desirable to have melt processable elastomeric compositions that may be preferentially crosslinked in a select phase of the composition.

It is further desirable to have macromolecular crosslinking agents capable of preferential crosslinking in a select phase of the composition and contributing to improved mechanical and elastic properties of the resulting elastomeric compositions.

It is also desirable to have elastomeric compositions that are suitable for forming elastomeric products, such as apertured or macroscopically-expanded three-dimensional elastomeric webs, or components of absorbent products (including health care products or personal hygiene products) or stretchable garments. The absorbent products may include taped/fastened diapers, pull-on diapers, training pants, incontinence garments, sanitary napkins, pantiliners, wipes, wound dressings, bandages, drapes and wraps.

SUMMARY OF THE INVENTION

The present invention is directed to a radiation-curable, low stress relaxation elastomeric composition with improved mechanical and elastic properties. The composition may comprise:
  a) from about 20 to about 80 wt % of a thermoplastic elastomer (TPE) which is a block copolymer having at least one hard block comprising vinylarenes and at least one soft block comprising dienes;
  b) from about 5 to about 60 wt % of a processing oil; and
  c) from about 1 to about 60 wt % of a macro photoinitiator;

wherein, after curing, the material has a stress relaxation of less than about 20 percent after 200% elongation at room temperature and a stress relaxation of less than about 45 percent after about 10 hours at 100° F. and 50% elongation.

The invention may further relate to elastomeric films, webs, and laminates made from the elastomeric compositions, as well as articles containing such films, webs or laminates.

All documents cited are, in relevant part, incorporated herein by reference; the citation of any document is not to be construed as an admission that it is prior art with respect to the present invention.

BRIEF DESCRIPTION OF THE DRAWINGS

While the specification concludes with claims particularly pointing out and distinctly claiming the subject matter of the present invention, it is believed that the present invention will be better understood from the following description taken in conjunction with the accompanying drawings in which like reference numerals identify identical elements and wherein:

DETAILED DESCRIPTION OF THE PRESENT INVENTION

Figure 1:
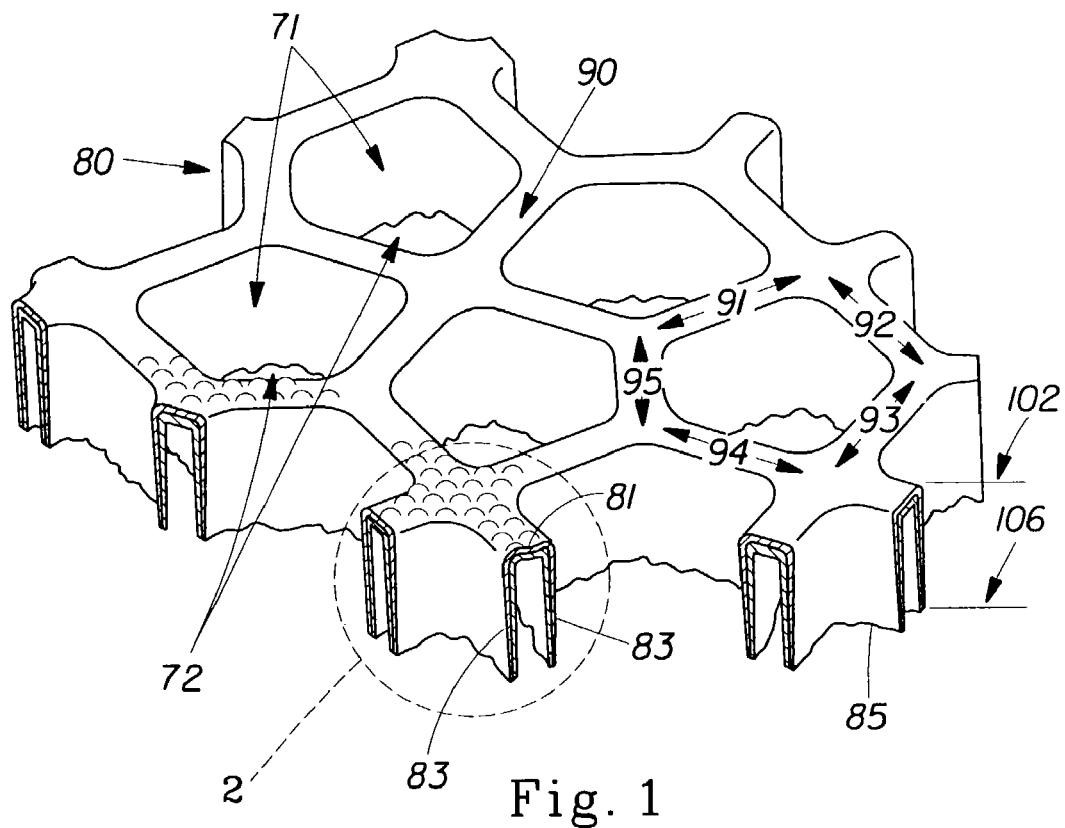
FIG. 1 is an enlarged, partially segmented, perspective illustration of an embodiment of a elastomeric web of the present invention having two layers of polymer film, at least one of which is elastomeric.

As used herein, the term "comprising" means that the various components, ingredient, or steps may be conjointly employed in practicing the present invention. Accordingly, the term "comprising" encompasses the more restrictive terms "consisting of" and "consisting essentially of".

As used herein, the terms "elastic" or "elastomeric" refer to any material which is capable of being elongated or deformed under an externally applied force, and which will substantially resume its original dimension or shape, sustaining only small permanent set (typically no more than about 20%), after the external force is released. The term "elastomer" refers to any material exhibiting elastic properties-as described hereinabove.

As used herein, the term "thermoplastic" refers to any material which may be melted and resolidified with little or no change in physical properties (assuming a minimum of oxidative degradation).

As used herein, the term "stretchable laminates" refers to multi-layer films, three-dimensional macroscopically-expanded webs or apertured webs made from such films, wherein at least one layer of the films or webs comprise an elastomeric material of the present invention. As used herein, the term "composite laminates" refers to the combinations of the preceding films/webs with fibrous nonwoven materials as well as combinations of monolithic films comprising the elastomeric material of the present invention with fibrous nonwoven materials.

All percentages, ratios and proportions used herein are by weight unless otherwise specified.

The present invention relates to a radiation-curable low stress relaxation elastomeric materials exhibiting improved elastic and mechanical properties, such as tensile modulus, ultimate elongation, and stress relaxation properties. The elastomeric material may be used in monolithic films or in multi-layer films having skin layers. The elastomeric films may be formed into apertured webs or macroscopically-expanded, three-dimensional, elastomeric webs. Further, the elastomeric films or webs may be joined to nonwoven fibrous webs and incrementally stretched (i.e., activated) to form elastomeric laminates. The elastomeric films, webs or laminates are suitable for use in elasticized or body-hugging portions of disposable absorbent articles such as side panels, waist bands, cuffs, or health care products such as dressings, bandages and wraps. The porous extensible polymeric webs or laminates of the present invention may also be used in other portions of the absorbent articles where a stretchable or breathable material is desired, such as topsheets or backsheets.

The elastomeric compositions of the present invention comprise an elastomeric block copolymer having least one hard block and at least one soft block, a macro photoinitiator, a processing oil, and optionally, a thermoplastic polymer and/or a crosslinking agent.

Suitable block copolymers for use herein may comprise at least one "hard" polymeric block and at least one "soft" polymeric block. Typically, the hard blocks (or the A blocks) are either amorphous and have a second order transition temperature or glass transition temperature above room temperature, or crystalline with a crystallizable segment (which may be in the backbone, in the side chain, or in the pendant groups) and have a first order transition temperature or crystalline melting temperature above room temperature. The definitions of these phase transitions can be found in *Principles of Polymer Chemistry*, by Flory, Cornell University Press (1953).

The soft blocks (or the B blocks) typically have a glass transition temperature below room temperature. The soft blocks are relatively mobile at room temperature. The hard blocks and the soft blocks tend to segregate from one another and form separate phases. These copolymers are generally referred to as thermoplastic elastomers (TPE's), wherein the hard blocks exhibit substantially thermoplastic characteristic and the soft blocks exhibit substantially elastomeric characteristic.

The hard block may comprise a polyvinylarene derived from monomers such as styrene, α-methyl styrene, para-methyl styrene, other alkyl styrene derivatives, or mixtures thereof. The hard block may also be a random copolymer derived from vinylarene monomers and short C2-C6 olefinic monomers such as ethylene, propylene, butylene, C4-C6 diene monomers such as isoprene, butadiene, or mixtures of diene/alkene monomers. In preferred embodiments, the hard block of the TPE comprises from about 1% to 20%, by weight of the hard block, of unsaturated or partially saturated dienes.

The hard block desirably has a number-average molecular weight between from about 1,000 to about 200,000, preferably from about 2,000 to about 100,000, more preferably from about 5,000 to about 60,000. The hard block may comprise from about 10% to about 80%, preferably from about 20% to about 50%, more preferably from about 25 to about 35% of the total weight of the block copolymer.

The soft block may be a diene polymer derived from unsaturated or partially saturated, diene monomers of from about 4 to about 6 carbons. Suitable diene monomers may include butadiene, isoprene, and the like. The soft block may also be an olefinic polymer derived from linear or branched alkene monomers of from about 2 to about 6 carbon atoms. Suitable alkene monomers may include ethylene, propylene, butylene, and the like. The soft block may also comprise a combination of the above monomers, such as ethylene/propylene polymers, ethylene/butylene polymers, and the like.

The number-average molecular weight of the soft block may be from about 1,000 to about 300,000, preferably from about 10,000 to about 200,000, and more preferably from about 20,000 to about 100,000. The soft block may comprise from about 20% to about 90%, preferably from about 50% to about 80%, more preferably from about 65% to about 75% of the total weight of the copolymer.

Suitable block copolymers for use herein may comprise at least one soft (i.e., substantially elastomeric) block portion B and at least one hard (i.e., substantially thermoplastic) block portions A. The block copolymers-may have multiple blocks, such as A-B-A triblock copolymers, A-B-A-B tetrablock copolymers, or A-B-A-B-A pentablock copolymers, and the like.

Also useful in the present invention are block copolymers having more than one A block and/or more than one B block, wherein each A block may be derived from the same or different vinylarene monomers and each B block may be derived from the same or different diene or olefinic monomers. For example, a triblock copolymer may have an elastomeric midblock B and two thermoplastic endblocks A and A', wherein A and A' may be derived from different vinylarene monomers.

In some embodiments, the olefinic block may comprise at least about 50 percent by weight of the block copolymer. The unsaturation in diene monomer may be selectively hydrogenated, if desired, to reduce sensitivity to oxidative degradation and may result in improved elastic and mechanical properties. For example, a polyisoprene block can be selectively reduced to form an ethylene-propylene block. In other embodiments, the vinylarene block may comprise at least about 10 percent by weight of the block copolymer. Higher vinylarene content provides low stress relaxation and high elastic/tensile properties.

Exemplary block copolymers may include styrene-diene-styrene or styrene-olefin-styrene triblock copolymers such as styrene-butadiene-styrene (S-B-S), styrene-ethylene/butylene-styrene (S-EB-S), styrene-ethylene/propylene-styrene (S-EP-S), styrene-isoprene-styrene (S-I-S), hydrogenated polystyrene-isoprene/butadiene-styrene (S-IB-S), and mixtures thereof. Commercially available block, copolymers include KRATON® from the Shell Chemical Company, Huston, Tex., SEPTON® from Kuraray America, Inc. New York, N.Y., and VECTOR® from Dexco Chemical Company, Houston, Tex.

The block copolymers may also be radial, having three or more arms, each arm being a copolymer having the structure of B-A, B-A-B-A, or the like, and the B blocks being at or near the center portion of the radial polymer.

The block copolymer may be used in the elastomeric composition in an amount effective to achieve the desired properties, such as tensile, elastic and stress relaxation and other mechanical properties. The block copolymer will generally be present in the elastomeric composition in an amount typically from about 20 to about 80 weight percent, preferably from about 25 to about 75 weight percent, and more preferably from about 30 to about 70 weight percent, of the composition.

The block copolymers used in this invention may-be end-group modified. By end-group modified, it is meant that polymers contain functional groups such as acrylate, alkylacrylate, maleates, fumarates, itaconate, citraconate, vinyl ether, vinyl ester, cinnamate, gamma-ketoacrylate, maleimide, hydroxyl, primary, secondary and tertiary amine, carboxyl, epoxy and thiol at one or two ends of the block copolymer. Examples of the synthesis of one-end group block copolymer are described in PCT patent publication WO99/64931, assigned to Dow Chemical and published on Dec. 16, 1999.

Preferred end-group modified polymers are the general form:
A-B-A-R
A-B-R
R-A-B-A-R
R'-A-B-A-R Where A is a styrene polymer block, B is a polymer block of ethylene/propylene, ethylene/butylenes, butadiene and/or isoprene, R and R' are end-groups as described above.

The photoinitiators may be functionalized macromolecules containing ultraviolet (UV) responsive substituents, which are prone to generate free radicals when exposed to a UV radiation. The resulting free radicals may abstract protons from the unsaturations in the TPEs to form radicals, which lead to chemical crosslinks between TPEs. These chemical crosslinks enhance the physical entanglements, resulting in strengthening of the three-dimensional network structure of the TPE matrix and improved elastic and mechanical properties. Additionally, the photoinitiators in their radical form may also react with one another and form an interpenetrating network with the TPE network that further enhances the elastic and mechanical properties of the resulting compositions.

Moreover, due to their macromolecular structures, the macromolecular photoinitiators (hereinafter "macro photoinitiators") may exhibit elastic and mechanical properties of a polymeric material. Thus, when the macro photoinitiators are blended with thermoplastic elastomers, they may enhance the elastic and mechanical properties of the blended compositions such that no additional thermoplastic materials may be needed to achieve the desired properties. The macro photoinitiators may be present in the amount ranging from about 1 to about 60 wt %, preferably from about 5 to about 50 wt % and more preferably from about 10 to about 40 wt % of the composition.

To target crosslinks in a desired phase of the TPEs, compatibility is a factor that may be considered. Whereas low molecular weight molecules generally mix well with both phases of the TPEs, high molecular weight polymeric materials may preferentially migrate into one phase which comprises more compatible polymeric blocks. Molecular weight and chemical structure are factors affecting compatibilities among polymers. Suitable macro photoinitiators for the present invention may have a number average molecular weight from about 5,000 to about 300,000, preferably from about 10,000 to about 200,000 and more preferably from about 25,000 to about 150,000. Structurally, macro photoinitiators containing aromatic or vinylarene monomeric units are more compatible with the hard phase of the TPEs and those containing aliphatic or olefinic monomeric units are more compatible with the soft phase of the TPEs.

Further, the macro photoinitiators comprise substituted monomers, which contain UV responsive substitutents. At least about 5%, preferably at least about 7% and more preferably at least about 10% of the monomeric units of a macro photoinitiator are substituted monomers, in order to produce a sufficient amount of crosslinks, which lead to improved elastic and mechanical properties. The substituted monomers may have the general structure:

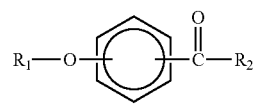

wherein $R_1$ may be vinyl, vinylarene, acrylate or methacrylate monomer and $R_2$ may be alkyl, aryl, alkylaryl, alkoxy, substituted alkyl, halogen, alkylsulphonates, alkylammonium sulphonates, peresters, cinnamates and tertiary amines. Macro photoinitiators may include, in the polymer backbone, substituted monomers having, but not limited to, the following exemplary structures:

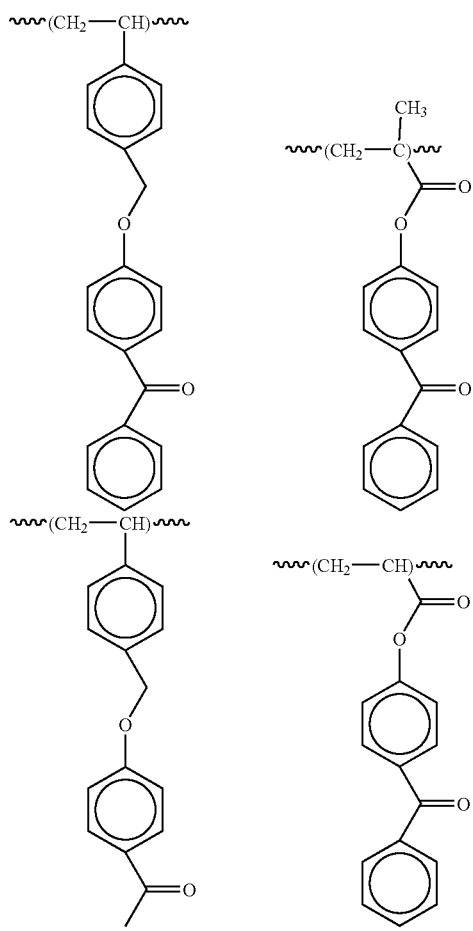
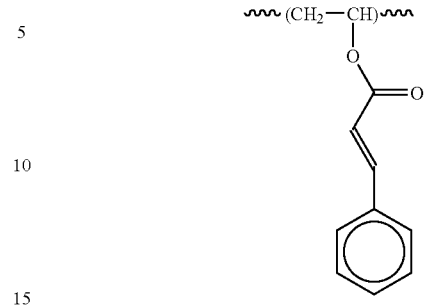

In one embodiment, the macro photoinitiator may be a substituted polystyrene containing acetophenone or benzophenone functional groups on the aromatic or aliphatic carbons of styrene and at least about 5% of the monomers are substituted.

In another embodiment, the macro photoinitiator may be prepared by grafting UV active groups into the polymer backbone which can be obtained from National Starch & Chemicals, Bridgewater, N.J., where the polymeric back bone may be any polymer with residual unsaturation repeat units. Useful polymers include, but are not limited to, styrene-butadiene-styrene (S-B-S), styrene-isoprene-styrene (S-I-S), polystyrene-isoprene/butadiene-styrene (S-IB-S), styrene-butadiene rubber (SBR), ethylene-propylene-dicyclopentadiene (EPDM), acrylonitrile butadiene styrene (ABS), polybutadiene (PBD), polyisoprene (PI) and mixtures there of.

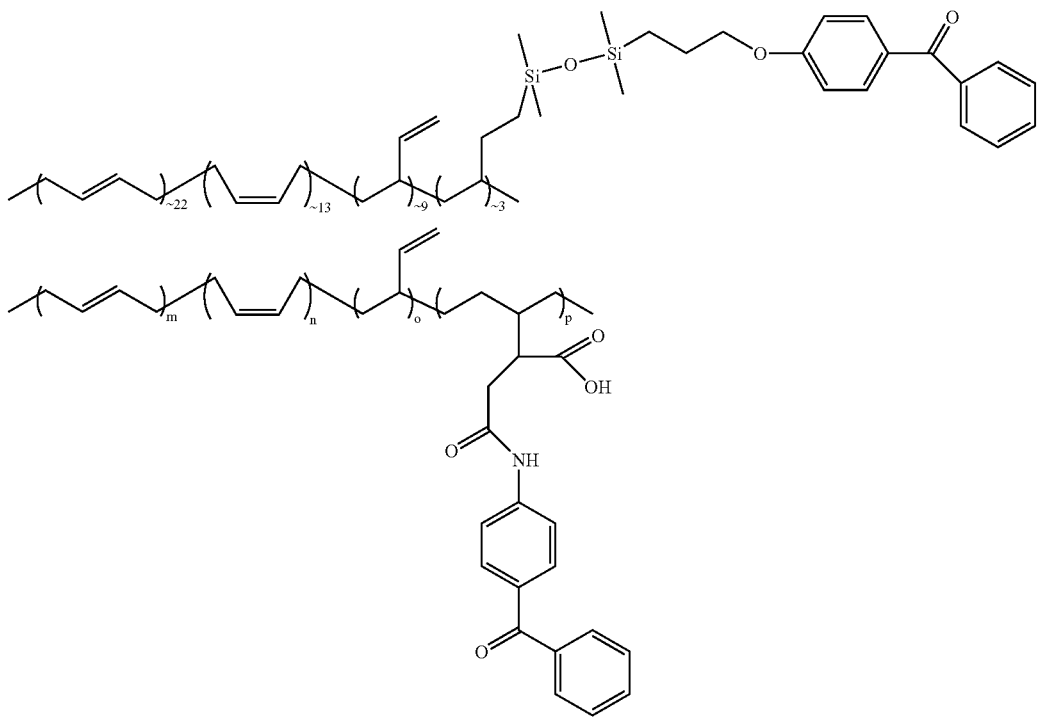

Optionally, crosslinking agents may also be used to speed up the crosslinking reaction. The crosslinking agents may contain multiple free radical receptive functionalities (typically with abstractable protons), which react with free radicals from the photoinitiators and/or other crosslinking agents. Thus, the multiple functionalities of the crosslinking agents may form multiple chemical crosslinks with the TPEs to and to improve the properties of the curable elastomeric composition. The molecular weight of the crosslinking agent may be low, typically less than about 700. Exemplary crosslinking agent may be a thiol, such as trimethylolpropane tris(3-mercaptopropionate); a di- or tri-acrylate, such as trimethylolpropane triacrylate; or a di- or tri-methacrylate, such as trimethylolpropane trimethacrylate all are available from Sigma-Aldrich Chemicals. In preferred embodiments, the low molecular weight crosslinking agents may be present in the amount ranging from about 0.5 to about 10 wt %, more preferably from about 1 to about 8 wt % and most preferably from about 1.5 to about 5 wt % of the composition.

Macromolecules containing both the UV responsive substitutents and the free radical receptive functionalities may also be suitable for use herein. Such macromolecules may function as photoinitiators as well as crosslinking agents. For example, the macro photoinitiators may contain unsaturated C=C in the backbone or in the substituents which contain abstractable protons that lead to additional chemical crosslinks.

Additionally, processing oils or plasticizing oils, such as a hydrocarbon oils, may be added to lower the viscosity and enhance the processability of the elastomeric compositions. However, processing oils tend to negatively affect the elastic, stress relaxation and tensile properties of the compositions. The typical range of the processing oil in the present elastomeric composition is from about 5 to about 60 wt %, preferably from about 10 to about 50 wt %, and more preferably from about 15 to about 45 wt % of the elastomeric compositions.

Typically, the processing oil is compatible with the composition, and is substantially non-degrading at the processing temperature. Suitable for use herein are hydrocarbon oils that are aliphatic (including linear, branched or cyclic) or aromatic. The oils may be mineral oil as well as other petroleum-derived oils and waxes, such as parafinic oil, naphthenic oil, petrolateum, microcrystalline wax, paraffin or isoparaffin wax. Synthetic waxes, such as Fischer-Tropsch wax; natural waxes, such as spermaceti, carnauba, ozokerite, beeswax, candelilla, paraffin, ceresin, esparto, ouricuri, rezowax; and other known mineral and mined waxes, are also suitable for use herein. Olefinic oligomers and low molecular weight polymers may also be used herein. The olefinic oligomers may be polypropylenes, polybutylenes, hydrogenated polyisoprenes, hydrogenated polybutadienes, or the like having a weight average molecular weight between about 350 to about 8000.

In a representative embodiment, the processing oil is a white mineral oil available under the tradename BRITOL® from Witco Company, Greenwich, Conn. In another representative embodiment, the processing oil is another mineral oil under the tradename DRAKEOL® from Pennzoil Company Penrenco Division, Karns City, Pa.

Optionally, various thermoplastic polymers or thermoplastic polymer compositions may be used in the elastomeric compositions of the present invention. In some embodiments, the thermoplastic polymers may preferentially associate with the hard blocks of the block copolymers and be incorporated into the entangled three-dimensional network structure of the hard phase. Not intending to be bound by theory, it is believed that this entangled network structure improves the tensile, elastic and stress relaxation properties. Thermoplastic polymers such as polyphenylene oxide, and vinylarene polymers derived from monomers including styrene, α-methyl styrene, para-methyl styrene, other alkyl styrene derivatives, vinyl toluene, and mixtures thereof, are useful in the present invention. Because they are generally considered to be chemically compatible with the styrenic hard blocks of the block copolymer. Compatible components may be more easily mix and incorporated into the entangled three-dimensional network structure, and they have a lower tendency to physically separate (i.e., disentangle) from the network structure.

It is advantageous to use polymers having high glass transition temperatures as the optional component in the elastomeric composition of the present invention. By having glass transition temperatures (Tg) higher than the use temperature of the elastomeric material, these polymers are relatively immobile at the use temperature and serve to "lock in" the three-dimensional network structure and provide the desired elastic and mechanical properties. As the gap between the use temperature and the glass transition temperature narrows, these polymers become more mobile. The mobile polymer chains may disentangle from the network structure, resulting in a weakened network structure and deteriorated elastic and mechanical properties. The stress relaxation properties are especially sensitive to such effects.

Moreover, for body temperature applications (such as absorbent articles, bandages, wraps, wound dressings, and the like) which may be worn next to a person's body for an extended period of time, it is beneficial to incorporate polymers having high glass transition temperatures, such as polyphenylene oxide or vinylarene polymers, into the elastomeric compositions. However, melt processability and processing temperature are factors to be considered as well. The former relates to ease of processing the elastomeric material and the applicability of various processing techniques. The latter relates to joining or applying the elastomeric material to other substrates or components having low thermal degradation temperatures (e.g., polyethylene) or delicate structures (e.g., a nonwoven web). Vinylarene polymers useful herein as optional component may typically have a glass transition temperature ranges from about 58° C. to about 180° C., more preferably from about 70° C. to about 150° C., more preferably from about 90° C. to about 130° C.

Thermoplastic polymers useful herein as the optional component may have an average molecular weight that is sufficiently high to provide high glass transition temperature, tensile and elastic properties. Further, these thermoplastic polymers may have an average molecular weight not significantly different from that of the hard blocks of the elastomeric block copolymers to achieve compatibility with the hard blocks. Suitable vinylarene polymers for use herein typically have a number-average molecular weight of about 600 to about 200,000, more preferably of about 5,000 to about 150,000, and most preferably from about 10,000 to about 100,000. Suitable vinylarene polymers may have a molecular weight distribution in the range of about 1 to about 4. In a representative embodiment, the vinylarene may be a polystyrene having a number-average molecular weight of about 40,000 to about 60,000, such as NOVACOR® PS 3900 series from Nova Chemicals, Inc., Monaca, Pa.

The thermoplastic polymers or compositions, when present, are typically in an amount from about 1 to about 60 weight percent, preferably from about 5 to about 40 weight percent, and more preferably from about 10 to about 30 weight percent of the low stress relaxation elastomeric composition used in the present invention.

The elastomeric compositions of the present invention may also comprise other additives such as antioxidants or stabilizers, anti-block or slip agents. Typical antioxidants are hindered phenols (i.e., those having sterically bulky groups, such as t-butyl groups, in the proximity of the phenolic hydroxyl group) or multi-functional phenols (i.e., those containing sulfur or phosphorous). A hindered phenol antioxidant IRGANOX® 1010 is available from Ciba-Geigy Company, Hawthorn, N.Y. Other additives may also be included in the elastomeric compositions, including, but not limited to, pigments, dyes, UV absorbers, odor control agents, perfumes, fillers, and desiccants. Each additive may be present in an amount less than about 10 wt %, preferably less than 5 wt % and more preferably less than 1 wt %.

The present invention also relates to films comprising the above elastomeric compositions. Further, the elastomeric film may contain one or more skin layers on its opposed surfaces to improve processability and handling of the film.

A typical skin layer may comprise polymers that are at least partially compatible or miscible with a component of the elastomeric block copolymers to provide sufficient adhesion between the elastomeric layer and the skin layer for further processing and handling.

Thermoplastic polymers suitable for use herein as the skin layer may be polyolefins derived from monomers such as ethylene, propylene, butylene; α-alkenes including 1-butene, 1-hexene, 1octene, and the like; polydienes derived from monomers such as isoprene, butadiene, 1,3-pentadiene and the like; and mixtures of these monomers; ethylene copolymers such as ethylene-vinylacetate copolymers (EVA), ethylene-methacrylate copolymers (EMA), and ethylene-acrylic acid copolymers; polyvinylarenes such as polystyrene, poly (cc-methyl styrene), styrenic random block copolymer (such as INDEX® interpolymers, available from Dow Chemicals, Midland, Mich.); polyphenylene oxide; and blends thereof.

The materials for the skin layer may have melt flow properties specifically suited for co-processing the skin material with the above elastomeric compositions to form a multi-layer film. A representative method to produce the multi-layer polymeric film is coextrusion. In one embodiment, the elastomeric composition is coextruded with the thermoplastic polymers to provide an elastomeric center layer between two skin layers, each being substantially facially joined to one of the opposing surfaces of the center layer. The two skin layers may have the same or different compositions.

Additionally, adhesives and/or tie layers may be used to promote adhesion between the center elastomeric layer and the thermoplastic skin layer. Each tie layer, when employed, may comprise from about 5 to 10 percent of the total film thickness.

Typically, the elastomeric layer itself is capable of undergoing from 50% to 1200% elongation at room temperature as a monolithic, non-apertured film. The elastomer layer may comprise either pure elastomers or elastomeric compositions. The elastomeric materials of the present invention may exhibit a stress relaxation at 200% elongation of less than about 20%, more preferably less than about 30%, and most preferably less than about 40% at room temperature. The elastomeric materials of the present invention exhibits a stress of less than about 45%, preferably less than about 50%, and more preferably less than about 55% relaxation, at 50% elongation after 10 hours at body temperature (about 100° F.).

The skin layer of the present invention is preferably thinner and substantially less elastic than the elastomeric layer. In some embodiments, the skin layers may even be inelastic. When the skin layers are used in conjunction with the elastomeric layer the resulting films or webs may have modified elastic properties that are different from those of the monolithic elastomer layer. If more than one skin layer is used, the skin layers may have the same or different material characteristics.

In a multi-layer film, the elastomeric layer may comprise from about 20% to about 95% of the total thickness of the film and each skin layer may comprise from about 1% to about 40% of the total thickness of the film. Typically, the elastomeric film (monolithic or multi-layer) has a thickness of from about 0.5 mils to about 20 mils, preferably from about 1.0 mil to 5.0 mils. Each skin layer is typically about 0.05 mil to about 5 mils thick, and preferably from about 0.1 mil to about 1.5 mils thick. In a representative embodiment, the elastomeric layer is about 3.2 mils thick and each skin layer is about 0.15 mil thick. In another representative embodiment, the elastomeric layer is about 3.2 to 3.0 mils thick and each skin layer is about 0.12 to 0.10 mil thick Also within the scope of the present invention is a macroscopically-expanded, three-dimensional web made from multi-layer polymeric films such as those described herein. Detailed descriptions of such webs are disclosed in U.S. Pat. No. 3,929,135 (Thompson); U.S. Pat. No. 4,342,314 (Radel et al.); U.S. Pat. No. 5,733,628 (Pelkie); U.S. Pat. No. 6,303, 208 (Pelkie); and PCT Publication WO 98/37266 (Curro et al.). Such three-dimensional web exhibits the advantages of high porosity and high elasticity, as well as reliability, and high strength.

FIG. 1 is a representative embodiment of a macroscopically-expanded, three-dimensional web 80 of the present invention. Web 80 exhibits a multiplicity of primary apertures 71, which are formed in plane 102 of the first surface 90 by a continuous network of interconnecting members, e.g., members 91, 92, 93, 94, 95 interconnected to one another. The shape of primary apertures 71 as projected on the plane of the first surface 90 are preferably in the shape of polygons, e.g., squares, hexagons, etc., in an ordered or random pattern. In another representative embodiment, each interconnecting member comprises a base portion 81 located in plane 102, and each base portion has a sidewall portion 83 attached to each edge thereof. The sidewall portions 83 extend generally in the direction of the second surface 85 of the web and intersect with side walls of adjoining interconnecting members. The intersecting sidewall portions are interconnected to one another intermediate the first and second surfaces of the web, and terminate substantially concurrently with one another to form a secondary aperture 72 in the plane 106 of the second surface 85.

Figure 2:
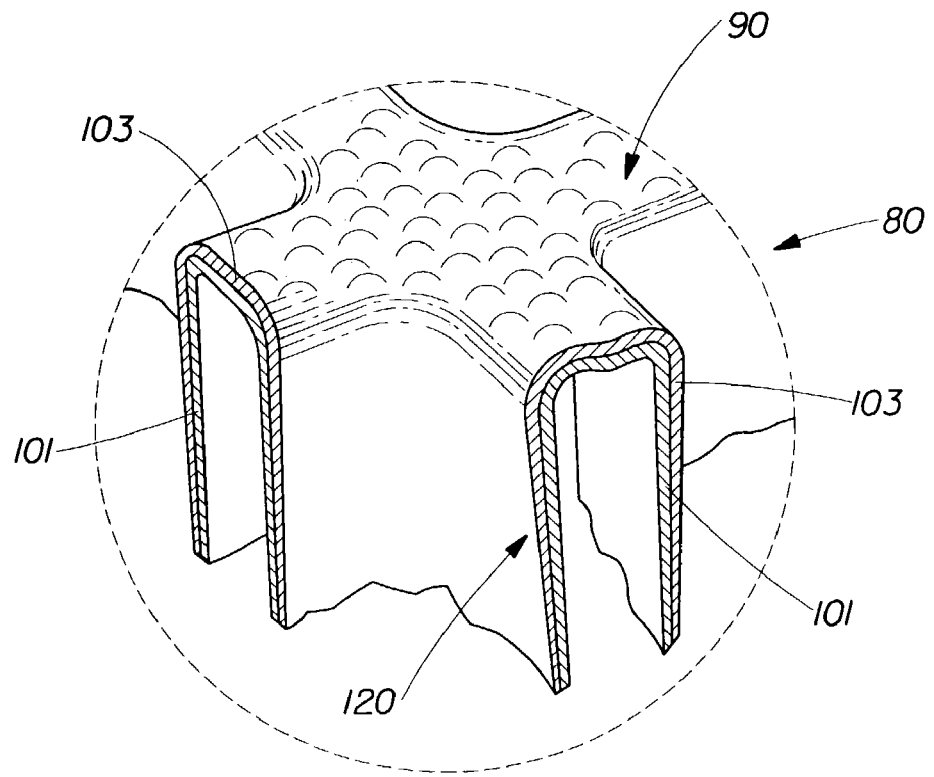
FIG. 2 is a further enlarged, partial view of a web of the type generally shown in FIG. 1, but illustrating in greater detail the web construction of an alternative elastomeric web of the present invention.

FIG. 2 is a further enlarged, partial view of a web of the type generally similar to web 80 of FIG. 1, but illustrating an alternative web construction according to the present invention. The multi-layer polymeric apertured film 120 of web 80 is preferably comprised of at least one elastomeric layer 101, and at least one skin layer 103. While FIG. 2 shows a two-layer embodiment with the skin layer 103 nearer the first surface 90, it is believed that the order of layering of the apertured film 120 is not limiting. Though in some embodiments, as shown in FIG. 2, the polymeric layers terminate substantially concurrently in the plane of the second surface, it is understood that it is not essential that they do so, i.e., one or more layers may extend further toward the second surface than the others.

The elastomeric film or web of the present invention may be used in disposable absorbent articles or health care products. It is understood that even stretchable garments such as undergarments, stockings, leggings, swimwear, and other sportswear, may benefit from the porous, extensible characteristics of an elastomeric film or web of the present invention.

Figure 3:
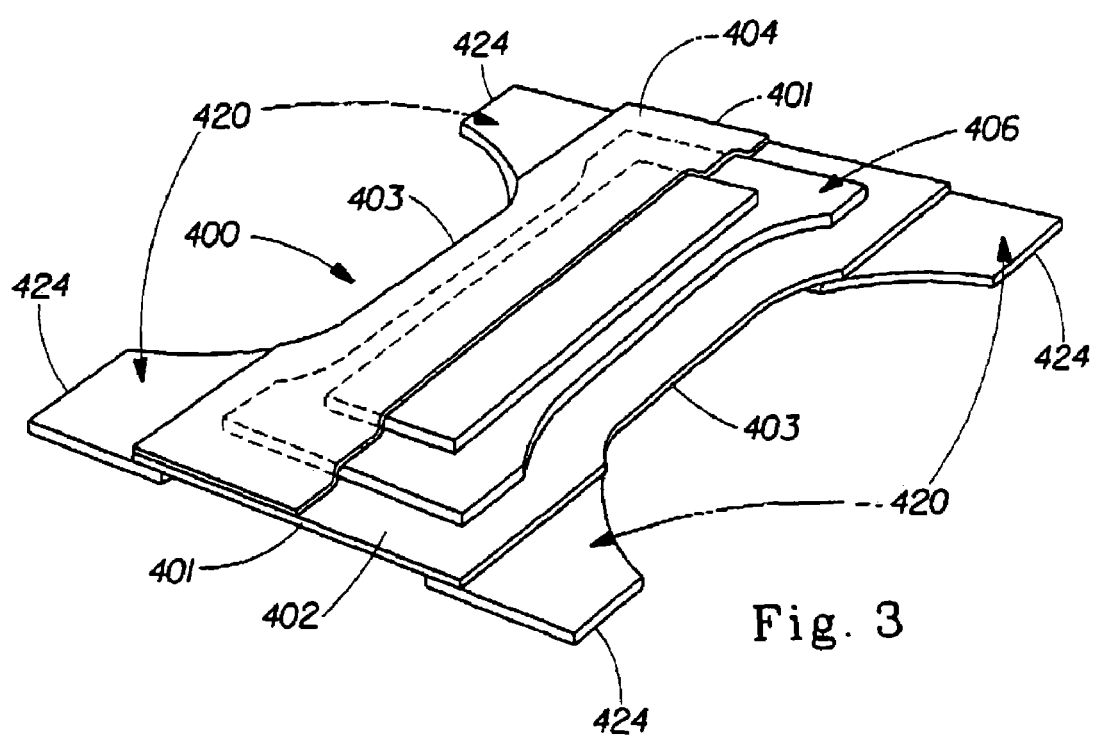
FIG. 3 is a partially segmented perspective illustration of a disposable garment, at least a portion of which comprises the elastomeric material of the present invention.
Figure 4:
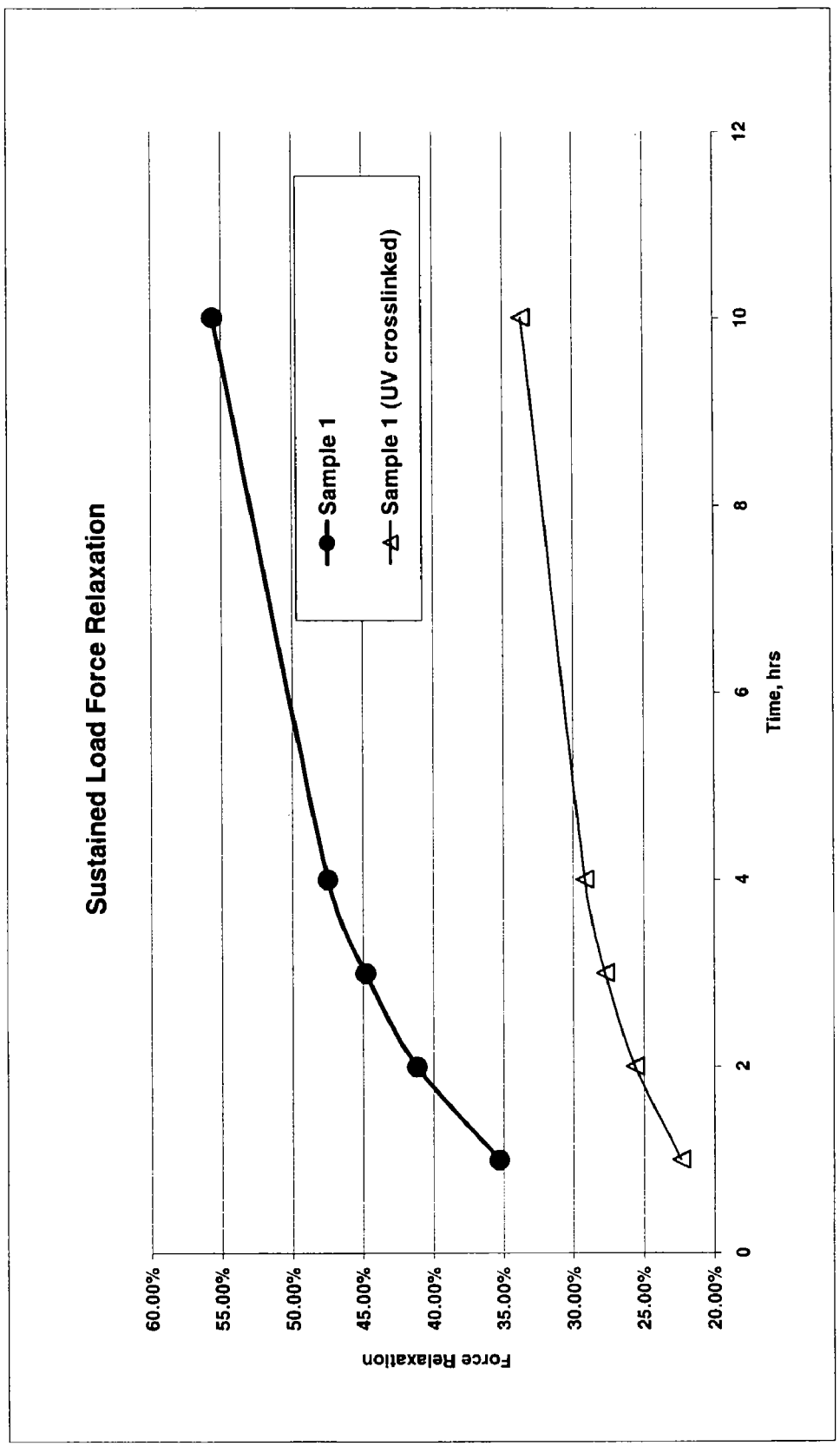
FIG. 4 is a plot of the sustained load force relaxation of Example 1 pre- and post-crosslinking.
Figure 5:
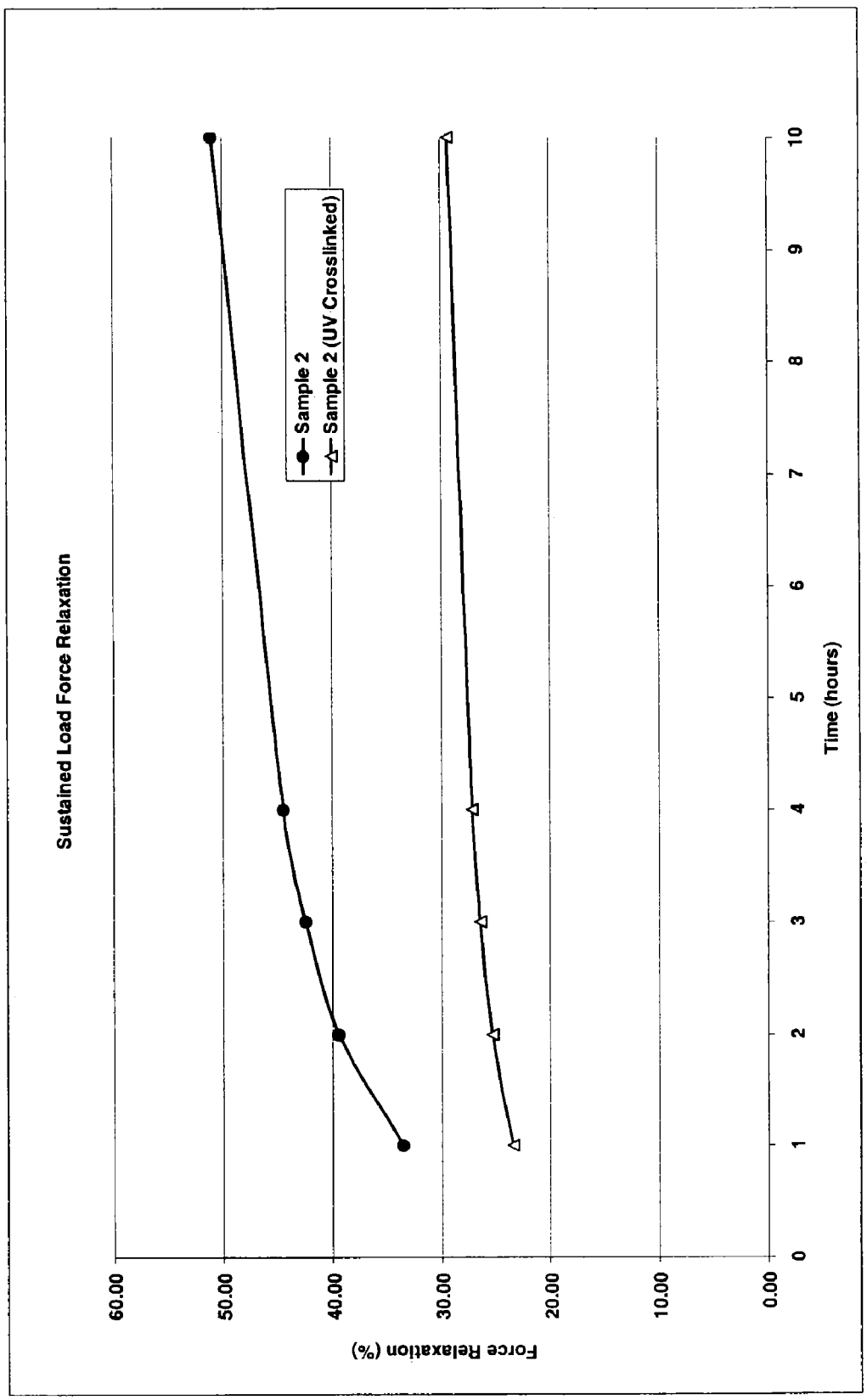
FIG. 5 is a plot of the sustained load force relaxation of Example 2 pre- and post-crosslinking.

A representative embodiment of a disposable absorbent article containing an elastomeric film or web made of the present elastomeric composition is shown in FIG. 3 in the form of a diaper 400 in a flattened state (i.e., prior to its being placed on a wearer). As used herein, the term "diaper" refers to a garment generally worn by infants and incontinent persons that is worn about the lower torso of the wearer. Exemplary diaper configurations are described generally in U.S. Pat. No. 3,860,003 (Buell); U.S. Pat. No. 5,151,092 (Buell et al.); U.S. Pat. No. 5,221,274 (Buell et al.); U.S. Pat. No. 5,554,145 (Roe et al.); U.S. Pat. No. 5,569,234 (Buell et al.); U.S. Pat. No. 5,580,411 (Nease et al.) and U.S. patent application Ser. No. 08/915,471, now U.S. Pat. No. 6,004,306 (Robles et al.).

FIG. 3 is a representative embodiment of the diaper 400 in which the topsheet 404 and the backsheet 402 are co-extensive and have length and width dimensions generally larger than those of the absorbent core 406. The topsheet 404 is joined with and superimposed on the backsheet 402 to form the periphery of the diaper 400. The periphery defines the outer perimeter or the edges of the diaper 400. The periphery comprises the end edges 401 and the longitudinal edges 403.

In one embodiment, the diaper may comprise a pair of elastomeric side panels 420, which extend laterally from end edges 401 of diaper 400 in an extended configuration. In an alternative embodiment, opposing sides 424 of the garment may be seamed or welded to form a pant. This allows the article to be used as a pull-on diaper or training pant. Exemplary diapers with elasticized side panels are disclosed in U.S. Pat. No. 4,857,067 (Wood et al.); U.S. Pat. No. 4,381,781 (Sciaraffa et al.); U.S. Pat. No. 4,938,753 (Van Gompel et al.); U.S. Pat. No. 5,151,092 (Buell); U.S. Pat. No. 5,221,274 (Buell); U.S. Pat. No. 5,246,433 (Hasse et al.); U.S. Pat. No. 5,464,401 (Hasse et al.); U.S. Pat. No. 5,669,897 (LaVon et al.); U.S. Pat. No. 5,897,545 (Kline et al.); U.S. Pat. No. 6,120,487 (Ashton) and U.S. patent application Ser. No. 08/155,048 (Roble et al.), now abandoned.

The elastomeric side panels 420 may comprise the elastomeric film or web of the present invention. In other embodiments, when the film or web of the present invention is used as the side panels, it may be further processed to form a composite laminate by bonding it on one, or both sides thereof, with fibrous nonwoven materials to form a laminate.

The elastomeric film or web of the present invention may also be used in other portions of the diaper, including elastic members adjacent the periphery of the diaper 400, such as the waist and leg openings, elastic topsheet or backsheet.

The multi-layer film 120 of the present invention may be processed using conventional procedures for producing multi-layer films on conventional coextruded film-making equipment. In general, polymers can be melt processed into films using either cast or blown film extrusion methods both of which are described in "Plastics Extrusion Technology" 2nd Ed., by Allan A. Griff (Van Nostrand Reinhold, 1976). Coextrusion processes are also described in U.S. Pat. Nos. 4,152,387, 4,197,069, 4,533,308, all are issued to Cloeren.

After the multi-layer elastomeric film has been coextruded, it is preferably fed to a forming process for aperturing, resulting in a macroscopically-expanded, three-dimensional, elastomeric web of the present invention. Such processes may include hydroforming, vacuum forming and are described in U.S. Pat. Nos. 3,929,135; 4,342,314; 4,154,240; 4,695,422; 4,552,709; 4,878,825; 4,741,877; 5,733,628 (Pelkie) and PCT Publication WO 98/37266 (Curro et al.). Other methods of aperturing planar, non-apertured elastomeric films are also known in the art, such as die punching, slitting and hot-pin melt aperturing. The monolithic or multi-layer films comprising the elastomeric compositions of the present invention may be formed into apertured webs using these methods.

The film or web may be further processed to form a composite laminate by bonding with fibrous nonwoven materials on one or both sides thereof, to form a laminate, using methods known in the art, such as adhesive, heat, pressure, or ultrasonic bonding. After bonding to a fibrous nonwoven material, the composite laminate may become less elastomeric than the elastomeric film or web alone, due to the relative inelasticity of the bonded nonwoven. To render the nonwoven more elastic, and to restore elasticity to the composite laminate, the composite laminate may be processed by methods and apparatus used for elasticizing "zero strain" laminates by an incremental stretching process, as disclosed in the aforementioned U.S. Pat. No. 5,143,679 (Weber et al.); U.S. Pat. No. 5,156,793 (Buell et al.) and U.S. Pat. No. 5,167,897 (Weber et al.). The resulting elasticized "zero-strain" composite laminate has a soft, compliant, cloth-like feel and a comfortable, snug fit when used in an absorbent article or other personal/health care products.

The radiation crosslinking may be performed with controlled UV radiation in the wavelength range of 250 to 400 nm and a dosage ranging from about 0.1 to about 10 J/cm$^2$, preferably from about 0.5 to about 8 J/cm$^2$ and more preferably from about 1 to about 5 J/cm$^2$. An equipment suitable for use herein may be a benchtop conveyor Model LC-6B available from INPRO Technologies, Inc., Fredrick, Md. The radiation crosslinking step is typically performed after the coextrusion and/or aperturing steps.

Test Method

A. Tensile Strength and Elongation at Failure

The properties determined by this method may correlate with the stretchability of the elastomeric film. These properties are relevant to the choice of material suitable for use as the elastic component of an absorbent article, particularly pull-on diapers, training pants, disposable diapers with fasteners, or other absorbent garments for adult use, that is substantially stretched when being put on.

A commercial tensile tester from Instron Engineering Corp., Canton, Mass. or SINTECH-MTS Systems Corporation, Eden Prairie, Minn. may be used for this test. The films are cut into 1" (2.54 cm) wide in MD (the machine direction of the film) by 2" (5.08 cm) long in CD (the cross direction which is at a 90° angle from MD) samples. The instrument is interfaced with a computer for controlling the test speed and other test parameters, and for collecting, calculating and reporting the data. The tensile stress-strain properties of the film are determined according to ASTM Method D882-83. These tensile properties are measured at room temperature (about 20° C.). The procedure is as follows:

(1) choose appropriate jaws and load cell for the test; the jaws should be wide enough to fit the sample, typically 1" (2.54 cm) wide jaws are used; the load cells is chosen so that the tensile response from the sample tested will be between 25% and 75% of the capacity of the load cells or the load range used, typically a 50 lb (22.7 kg) load cell is used;

(2) calibrate the instrument according to the manufacture's instructions;

(3) set the gauge length at 1" (2.54 cm);

(4) place the sample in the flat surface of the jaws according to the manufacture's instructions;

(5) set the cross head speed at a constant speed of 10"/min (0.254 m/min);

(6) start the test and collect data simultaneously; and (7) calculate and report tensile properties including elongation at break, and load at 100%, 200% and 300% elongation. The average result of three samples is reported.

B. Sustained Load Stress Relaxation Test

The property determined by this method may correlate with the elastic forces experienced by a wearer while wearing a product having elastic components, such as a side panel, a waist band, and the like, specifically how the product fits at body temperature after it has been worn for an extended period of time. The property determined by this method is relevant to the choice of materials that resist stress relaxation under sustained load at body temperature (approximately 100° F.), hence provide sustained fit over a long wear time of an absorbent article.

The instrument and the sample are the same as Test Method A above. The sustained load stress relaxation is measured at 100° F. (about human body temperature). The procedure is as follows:

(1) choose appropriate jaws and load cell for the test; the jaws should be wide enough to fit the sample, typically 1" (2.54 cm) wide jaws are used; the load cells is chosen so that the response from the sample tested will be between 25% and 75% of the capacity of the load cells or the load range used, typically a 50 lb (22.7 kg) load cell is used;
(2) calibrate the instrument according to the manufacturer's instructions;
(3) set the gauge length at 1" (2.54 cm) and place the sample in the instrument according to the manufacturer's instructions
(4) set the cross head speed at a constant speed of 10"/min (0.254 m/min);
(5) Prestrain the sample to 500% elongation and immediately (i.e., without holding time) return to 0% elongation;
(6) Reclamp the prestrained sample to remove any slack and maintain a 1" (2.54 cm) gauge length;
(7) Start the sustained load stress relaxation test and collect data simultaneously, the sustained load stress relaxation test has the following steps:
  a) go to 200% elongation at a rate of 10"/min (0.254 m/min);
  b) hold position for 30 seconds;
  c) go to 0% elongation at the at a of 10"/min (0.254 m/min);
  d) hold position for 60 seconds;
  e) go to 50% elongation at a rate of 10"/min (0.254 m/min);
  f) hold position for 10 hours; and
  g) go to 0% elongation; and
  h) calculate the stress relaxation at 50% elongation as the % loss between the initial load and the load at time t of step 7(f) as follows:

$$\% \text{ Force Relaxation at time, } t = \frac{[(\text{initial load}) - (\text{load at time, } t)]}{(\text{initial load})} \times 100$$

The average result of three samples is reported.

C. Hysteresis or Stress Relaxation Test

The property determined by this method may correlate with the forces a wearer experiences from an elastic component incorporated into a product. The first cycle is a prestraining step that simulates the conditions the elastic component experiences as the product is initially stretched in order to put the product on a wearer or to adjust the product to fit the wearer. The second cycle measures the reduction in elastic forces (i.e., stress relaxation) resulting from the prestraining step.

The instrument and the sample are the same as Test Method A above. The test procedure is similar to Test Method B above, except for the following modifications: (1) the test is done at room temperature (about 20° C.); (2) the test terminates after step 7(c); and (3) the stress relaxation at 200% elongation is calculated as the % loss between the initial load and the final load of step 7(b). The unload stress at 50% and 30% elongation during step 7(c) is reported.

While particular embodiments of the present invention have been illustrated and described, it would be apparent to those skilled in the art that various other changes and modifications can be made without departing from the spirit and scope of the invention. It is therefore intended to cover in the appended claims all such changes and modifications that are within the scope of this invention.

EXAMPLES

Examples 1-4

A formulation is prepared by blending varying amounts of a styrenic elastomeric copolymer such as Vector 4211, Vector 8505 series form Dexco Company, Houston, Tex., a 70/30 blend of S-B-S/methacrylate modified S-B (SB-MA) from Dexco Company, Houston, Tex., a vinylarene resin such as polystyrene PS3900 from Nova Chemical, Inc. Monaca, Pa., a macro photoinitiator from National Starch and Chemicals Bridgewater, N.J., and mineral oil such as Drakeol® available from Pennzoil Co., Penrenco Div., Karns City, Pa., to form an elastomeric mixture.

The compounded formulations are prepared by dry blending the polymeric components and oil for at least 24 hours. A Haake batch mixer compounder is pre-heated to 150° C. and the dry blend formulation is added slowly into the compounder. In some cases, some of the components are in form of viscous liquid, which are added to the polymeric components and oil mixture via pipettes directly during the compounding procedure.

Examples of the elastomeric composition suitable for use herein are shown in Table 1. The amount of each component is expressed in weight percent of the elastomeric composition. Additives, specifically antioxidants, which are present only in small amounts, are not shown in the compositions of TABLE 1. Typically, the elastomeric compositions useful in the present invention comprise about 0.5 wt % of antioxidants and about 0.3 wt % of light stabilizers.

TABLE 1

| Elastomeric Compositions (Weight Percent) | | | | |
|---|---|---|---|---|
| Example | 1 | 2 | 3 | 4 |
| S-I-S | 43 | 72 | 43 | 0 |
| S-B-S | 0 | 0 | 29 | 72 |
| SBS/SB-MA | 28 | 0 | 0 | 0 |
| Polystyrene PS3900 | 15 | 15 | 15 | 15 |
| Mineral Oil | 10 | 8 | 8 | 8 |
| Macro photoinitiator | 4 | 5 | 5 | 5 |

The physical properties of pressed films (compression molded) are determined prior to and after the exposure to UV irradiation.

The films are prepared by weighing approximately 12 grams of compounded formulation. The formulation is compression molded by placing the pre-weighed formulation between two pieces of PTFE (Teflon) film (0.010 in thick), which is then placed between preheated aluminum plates that are inserted into a Carver Press model 3853-0 with heated plates set to approximately 168° C. The formulation is allowed to heat up for 3 minutes and then it is pressed between the plates with an applied pressure of 2500 psi. The formulation is allowed to flow under pressure for 30 seconds. The resulting film is then quenched to ambient temperature and subsequently cut into three equal portions. Each portion is placed between films of PTFE and preheated aluminum plates and allowed to heat up to 168° C. for 1 minute in the Carver press before 2,000 psi of pressure is applied. The formulation is allowed to flow under this pressure for 30 seconds. The pressure is removed and the sample is rotated 90° and inserted back into the press and immediately 3,000 psi of pressure is applied. The formulation is again allowed to flow for 30 seconds. The pressure is removed and the sample is flipped and inserted back into the press and immediately 4,000 psi of pressure is applied. The formulation is again allowed to flow for 30 seconds. The pressure is removed and the sample is rotated 90° and inserted back into the press and immediately 5,000 psi of pressure is applied. The formulation is again allowed to flow for 30 seconds. After the final pressing, the film is quenched to ambient temperature. The resulting film thickness is between 4 mils up to 10 mils thick. The films are cut into proper sample size according to the test methods described hereinabove.

A benchtop conveyor Model LC-6B available from INPRO Technologies, Inc., Fredrick, Md. is used to UV irradiate the cut films for crosslinking studies and compared to the uncrosslinked corresponding films. The UV crosslinking is done by placing the films on the moving conveyor belt at the speed of approximately 54-feet/min. under the UV source. This step is repeated 4 times to achieve approximately 1.4 to 2.5 J/cm² of UV dosage.

The physical properties of Examples 1 and 2 prior to and after UV Irradiation are disclosed in TABLES 2 and 3.

TABLE 2

Tensile Strength Data

| Example | Stress @ 100% (MPa) | Stress @ 200% (MPa) | Stress @ 300% (MPa) | Elongation @ Break (%) |
|---|---|---|---|---|
| 1a | 0.43 | 0.57 | 0.76 | 818 |
| 1b (UV crosslinked) | 0.89 | 1.75 | 3.21 | 830 |
| 2a | 1.37 | 1.89 | 2.80 | 780 |
| 2b (UV crosslinked) | 2.10 | 3.69 | 5.36 | 900 |

TABLE 3

Hysteresis and Sustained Load Force Relaxation Data

| Example | Stress @ 50% (MPa) | Stress @ 200% (MPa) | Force relaxation @ 200% (%) | Stress @ 50% (unload) (MPa) | Stress @ 30% (unload) (MPa) | 10 Hours Stress Relaxation @ 50% @ 100 F. (%) |
|---|---|---|---|---|---|---|
| 1a | 0.35 | 0.58 | 9.4 | 0.21 | 0.13 | 56 |
| 1b (UV crosslinked) | 0.60 | 1.33 | 12.8 | 0.41 | 0.27 | 34 |
| 2a | 0.54 | 1.02 | 9.1 | 0.36 | 0.26 | 51 |
| 2b (UV crosslinked) | 0.78 | 1.97 | 13.4 | 0.41 | 0.25 | 29 |

As can be seen in Tables 2 and 3, the tensile strength and hysteresis of UV irradiated Examples 1 and 2 are increased while the sustained load force relaxation of these samples are substantially reduced when compared to the uncrosslinked versions of Examples 1 and 2.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A melt-blended radiation-curable material comprising:
   (a) from about 20 to about 80 wt % of a thermoplastic elastomer (TPE) which is a block copolymer having at least one hard block comprising vinylarenes and at least one soft block comprising dienes;
   (b) from about 5 to about 60 wt % of a processing oil; and
   (c) from about 5 to about 60 wt % of a macro photoinitiator having a number average molecular weight of from about 5,000 to about 300,000, wherein the macro photoinitiator is selected from the group consisting of:

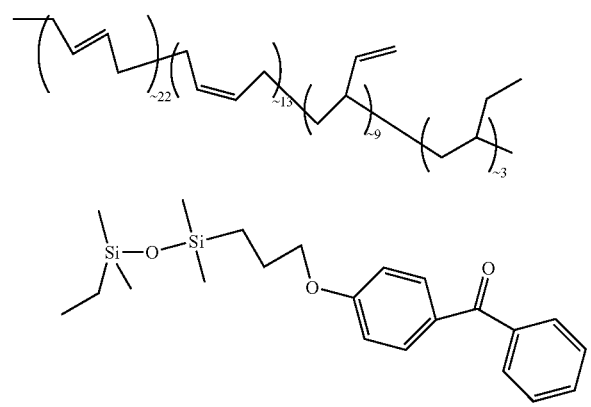

and

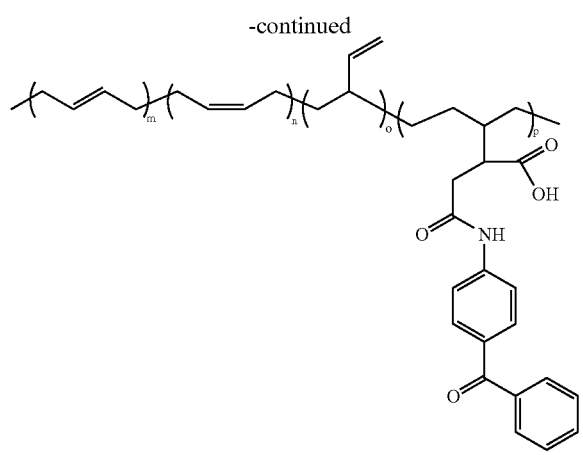

wherein, after curing, the material has a stress relaxation of less than about 20 percent after 200% elongation at room temperature and a stress relaxation of less than about 45 percent after about 10 hours at 100° F. and 50% elongation.

2. The material of claim 1 wherein the macro photoinitiator comprises monomers selected from the group consisting of, isoprene, butadiene and mixtures thereof.

3. The material of claim 1 wherein at least about 5% of the monomer units of the macro photoinitiator are substituted monomers with reactive substituents.

4. The material of claim 1 wherein the hard block of the TPE comprises vinylarene monomers selected from the group consisting of styrene, α-methyl styrene, para-methyl styrene, other alkyl styrene derivatives, and mixture thereof; and the soft block of the TPE comprises diene monomers selected from the group consisting of isoprene, butadiene, partially saturated dienes thereof, and mixtures thereof.

5. The material of claim 4 wherein the hard block comprises from about 10% to about 80% of the total weight of the block copolymer.

6. The material of claim 4 wherein the hard block of the TPE further comprises from about 1% to about 20%, by weight of the hard block, of unsaturated or partially saturated dienes.

7. The material of claim 1 wherein the block copolymer is end-group modified.

8. The material of claim 1 wherein said material further comprises from about 0.5 to about 10 wt % of a crosslinking agent.

9. The material of claim 1 wherein said material further comprises from about 1 to about 60 wt % of a thermoplastic polymer composition which comprises a polyvinylarene.

10. The material of claim 1 wherein the processing oil is selected from the group consisting of hydrocarbon oils, petroleum-derived oils and waxes, synthetic waxes, natural waxes, mineral or mined waxes, olefinic oligomers, and mixtures thereof.

11. The material of claim 1 wherein the crosslinking agent is a thiol, a diacrylate, a triacrylate, a dimethacrylate or a trimethacrylate.

12. The material of claim 1 wherein the material is cured by ultraviolet radiation.

13. An article to be worn adjacent to a person's body, at least a portion of the article comprising a stretchable laminate which comprises an elastomeric layer having opposed first and second surfaces and at least a first skin layer joined to the first surface of the elastomeric layer, wherein the elastomeric layer comprises:
(a) from about 20 to about 80 wt % of a thermoplastic elastomer (TPE) which is a block copolymer having at least one hard block comprising vinylarenes and at least one soft block comprising dienes;
(b) from about 5 to about 60 wt % of a processing oil; and
(c) from about 1 to about 60 wt % of a macro photoinitiator having a number average molecular weight of from about 5,000 to about 300,000, wherein the macro photoinitiator is selected from the group consisting of:

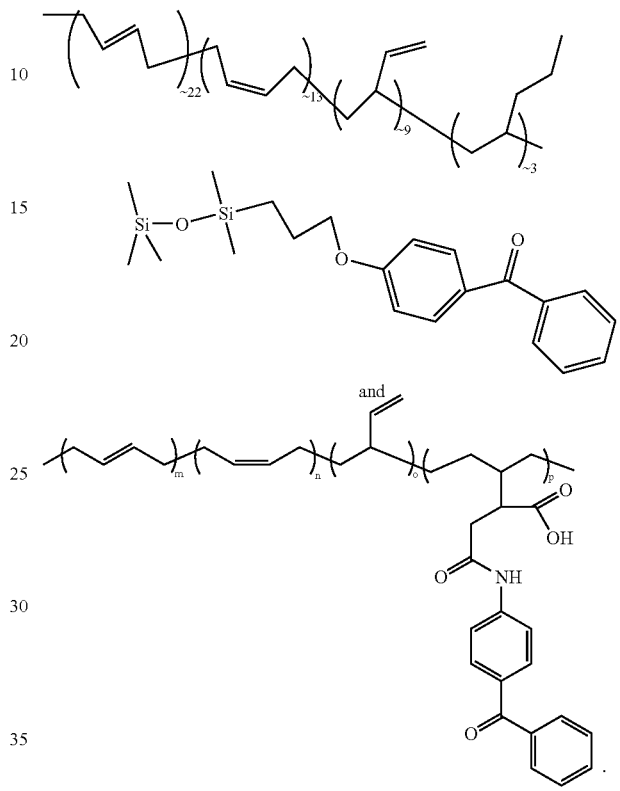

14. The article of claim 13 wherein the stretchable laminate further comprises a second skin layer joined to the second surface of the elastomeric layer.

15. The article of claim 14 wherein the first and second skin layers are the same or different, and comprise a thermoplastic polymer selected from the group consisting of polyolefins, α-alkene polymers, polydienes, ethylene copolymers, polyvinylarenes, polyphenylene oxide, and mixtures thereof.

16. The article of claim 13 wherein the stretchable laminate is a multi-layer film, a three-dimensional macroscopically-expanded web or an apertured web.

17. The article of claim 13 wherein the stretchable laminate is joined to a fibrous nonwoven material on an open surface of the first skin layer to form a composite laminate.

18. The article of claim 13 wherein the portion of the article is selected from the group consisting of a side panel, a leg elastic member, a waist elastic member, an elastic topsheet, an elastic backsheet, and combinations thereof.

19. The article of claim 13 wherein the article is a taped/fastened diaper, a pull-on diaper, training pants, an incontinence garment, a sanitary napkin, a pantiliner, a wipe, a wound dressing, a bandage, a drape, a wrap, a swimwear, a sportswear, a stocking, a legging or an undergarment.

20. A coextruded, UV curable elastomeric film, said film comprising an elastomeric layer and at least one thermoplastic skin layer joined to the elastomeric layer, said elastomeric layer comprising:
(a) from about 20 to about 80 wt % of a thermoplastic elastomer (TPE) which is a block copolymer having at least one hard block comprising vinylarenes and at least one soft block comprising dienes;

(b) from about 5 to about 60 wt % of a processing oil; and
(c) from about 1 to about 60 wt % of a macro photoinitiator having a number average molecular weight of from about 5,000 to about 300,000, wherein the macro photoinitiator is selected from the group consisting of :

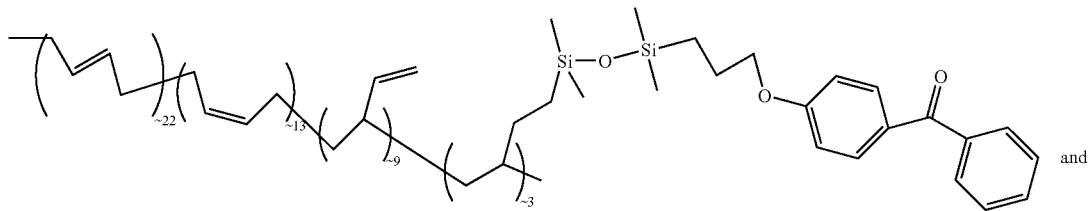
and

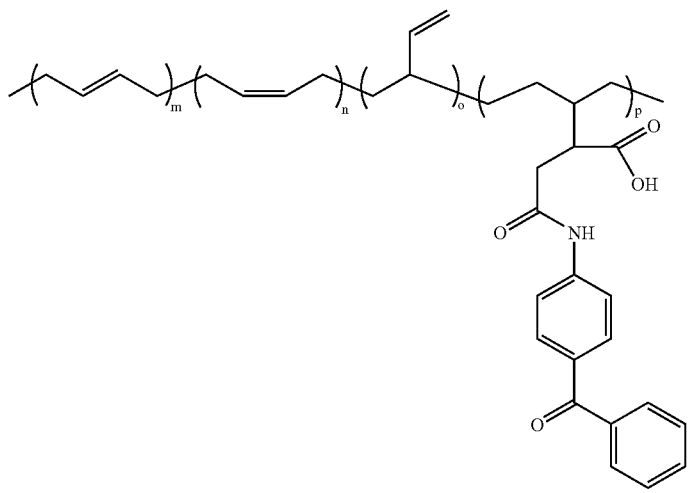

wherein the film is UV cured after coextrusion and has a stress relaxation of less than about 20 percent after 200% elongation at room temperature and a stress relaxation of less than about 45 percent after about 10 hours at 100° F. and 50% elongation.

21. A process for producing a stretchable laminate comprising the steps of:

(a) co-extruding an elastomeric material and a thermoplastic polymer to form a stretchable laminate, which comprises an elastomeric core layer and at least one thermoplastic skin layer, wherein the elastomeric material comprises a block copolymer having at least one hard block comprising vinylarenes and at least one soft block comprising dienes, a processing oil, and a macro photoinitiator having a number average molecular weight of from about 5,000 to about 300,000, wherein the macro photoinitiator is selected from the group consisting of:

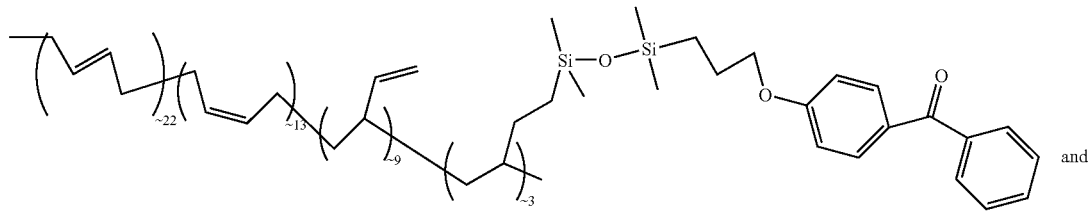
and

-continued

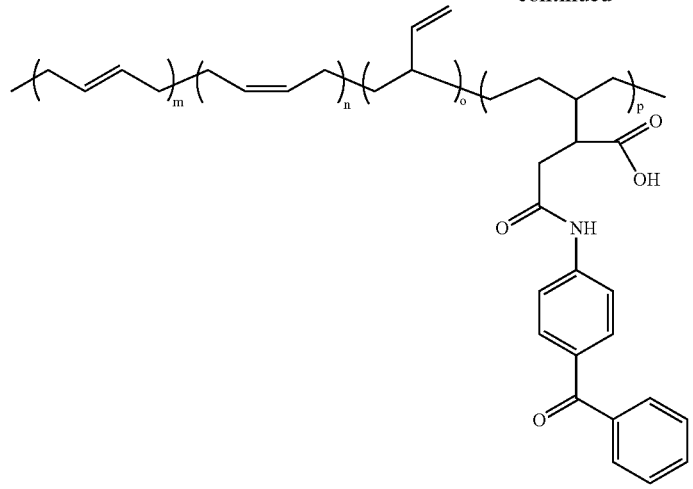

and
(b) radiation cross-linking the stretchable laminate to effectuate a sufficient amount of crosslinks to improve the stress relaxation properties of the elastomeric film.

22. The process of claim 21 which further comprises the step of aperturing the stretchable laminate.

23. The process of claim 21 wherein the process further comprises the step of joining a free surface of the skin layer to a fibrous nonwoven material to form a composite laminate.

24. The process of claim 21 wherein the process further comprises the step of incrementally stretching at least a portion of the composite laminate to permanently elongate the fibrous nonwoven material in the portion being stretched.

* * * * *